(12) United States Patent
Wei et al.

(10) Patent No.: US 11,300,446 B2
(45) Date of Patent: Apr. 12, 2022

(54) OPTICAL DETECTION METHOD AND OPTICAL DETECTION APPARATUS FOR FATIGUE STATE, AND OPTICAL DETECTION DEVICE

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventors: Pengfei Wei, Beijing (CN); Wei Sun, Beijing (CN); Zheng Jia, Beijing (CN); Xu Guan, Beijing (CN); Zhenwei Gao, Beijing (CN); Xue Gao, Beijing (CN); Ning Xie, Beijing (CN); Xingge Jia, Beijing (CN); Zongyuan Wang, Beijing (CN); Chuanhui Ma, Beijing (CN)

(73) Assignees: BEIJING BOE OPTOELECTRONICS TECHNOLOGY CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 44 days.

(21) Appl. No.: 16/683,511

(22) Filed: Nov. 14, 2019

(65) Prior Publication Data

US 2020/0309594 A1    Oct. 1, 2020

(30) Foreign Application Priority Data

Mar. 29, 2019 (CN) .......................... 201910250599.7

(51) Int. Cl.
*G01J 1/44* (2006.01)
*H01L 27/146* (2006.01)
(Continued)

(52) U.S. Cl.
CPC ................. *G01J 1/44* (2013.01); *A61B 3/113* (2013.01); *G06F 3/013* (2013.01);
(Continued)

(58) Field of Classification Search
CPC ......... G01T 1/44; H01L 27/146; H01L 27/49; H01L 27/14621; H01L 27/14609;
(Continued)

(56) References Cited

U.S. PATENT DOCUMENTS 5,790,234 A * 8/1998 Matsuyama ........... G03B 13/02
                                                    351/210
10,506,964 B2  12/2019 Li
(Continued)

FOREIGN PATENT DOCUMENTS

CN       203885510 A   10/2014
CN       104757981 A    7/2015
(Continued)

OTHER PUBLICATIONS

"Determination of the intensity of light reflected from the pupillary region, iris region, conjunctiva and eyelid interface of the normal eye", China Academic Journal Electronic Publishing House, http://www.cnki.net, 1985, 03, 006, pp. 16-19 with English translation of relevant parts (5 pages).
(Continued)

*Primary Examiner* — Hugh Maupin
(74) *Attorney, Agent, or Firm* — Collard & Roe, P.C.

(57) ABSTRACT

Disclosed are an optical detection method and an optical detection apparatus for a fatigue state of a user, and an optical detection device, this application relates to the field of detection technology, and is for improving accuracy of detection of the fatigue state. An optical detection method includes: irradiating eyes of the user with an infrared light; obtaining an intensity of an infrared light reflected by the
(Continued)

eyes of the user; and determining whether the user is in a fatigue state based on the intensity of the reflected infrared light.

9 Claims, 5 Drawing Sheets

(51) Int. Cl.
  *A61B 3/113* (2006.01)
  *G06F 3/01* (2006.01)
  *H01L 27/15* (2006.01)

(52) U.S. Cl.
  CPC .. *H01L 27/14609* (2013.01); *H01L 27/14621* (2013.01); *H01L 27/14649* (2013.01); *H01L 27/15* (2013.01)

(58) Field of Classification Search
  CPC H01L 27/15; A61B 5/163; A61B 5/18; A61B 3/113; G08B 21/06; G06F 3/013
  See application file for complete search history.

(56) References Cited

U.S. PATENT DOCUMENTS

| | | | |
|---|---|---|---|
| 10,817,721 | B2 | 10/2020 | Wilson |
| 2006/0065833 | A1* | 3/2006 | Craig ............... H01L 31/18 250/338.4 |
| 2009/0321666 | A1* | 12/2009 | Hilgers ............... H01L 27/1443 250/552 |
| 2010/0245093 | A1* | 9/2010 | Kobetski ............ G06K 9/00597 340/576 |
| 2018/0068160 | A1* | 3/2018 | Wu .................... G06K 9/00201 |
| 2018/0333092 | A1 | 11/2018 | Roshan et al. |
| 2019/0095672 | A1* | 3/2019 | Yeke Yazdandoost ...................... H01L 27/1462 |

FOREIGN PATENT DOCUMENTS

| | | | |
|---|---|---|---|
| CN | 105006105 A | 10/2015 | |
| CN | 105049596 A | 11/2015 | |
| CN | 105701971 A | 6/2016 | |
| CN | 105759945 A | 7/2016 | |
| CN | 106797422 A | 5/2017 | |
| CN | 107248263 A | 10/2017 | |
| CN | 107507395 A | 12/2017 | |
| CN | 108128241 A | 6/2018 | |
| WO | WO-2013179178 A1 * | 12/2013 | ............... A61B 3/10 |

OTHER PUBLICATIONS

Wang et al., "Research on the basic characteristics and application teaching photosensitive sensor", Experimental Technology and Management, May 2017, vol. 34, No. 5, pp. 171-173 and 177 with English translation of relevant parts (7 pages).

Chinese Office Action in Chinese Application No. 201910250599.7 dated May 28, 2021, with English translation.

* cited by examiner

OPTICAL DETECTION METHOD AND OPTICAL DETECTION APPARATUS FOR FATIGUE STATE, AND OPTICAL DETECTION DEVICE

The present application claims the priority of Chinese patent application No. 201910250599.7 filed on Mar. 29, 2019, the disclosure of which is incorporated herein by reference in its entirety as a part of the present application.

TECHNICAL FIELD

The present disclosure relates to the field of detection technology, and more particularly, to an optical detection method and an optical detection apparatus for a fatigue state of a user, and an optical detection device.

BACKGROUND

With the rapid development of the vehicle industry, vehicles have gradually entered every family, people are paying more and more attention to driving safety when driving vehicles. When people are driving, especially on long distances, fatigue driving often occurs, which causes a great threat to people's driving safety. At present, there are many types of fatigue driving detection apparatus, they generally detect the grip force on the steering wheel, and judge a fatigue degree of the driver through a magnitude of the grip force, but the accuracy of this detection mode is low.

SUMMARY

In view of the above, the embodiments of the present disclosure provide an optical detection method and an optical detection apparatus for a fatigue state of a user, and an optical detection device, with the primary objective to improve accuracy of the detection of a fatigue state.

In order to achieve the above objective, the present disclosure mainly provides the following technical solutions:

According to one aspect of present disclosure, provided is an optical detection method for a fatigue state of a user, comprising: irradiating eyes of the user with an infrared light; obtaining an intensity of an infrared light reflected from the eyes of the user; and determining whether the user is in a fatigue state based on the intensity of the reflected infrared light.

Optionally, determining whether the user is in a fatigue state based on the intensity of the reflected infrared light comprises: in a case where the time period during which the intensity of the reflected infrared light is less than a first threshold lasts for a first preset time period, determining that the user is in a fatigue state.

Optionally, determining whether the user is in a fatigue state based on the intensity of the reflected infrared light comprises: calculating a time period during which the intensity of the reflected infrared light is less than a second threshold, obtaining a blink time period according to the time period during which the intensity of the reflected infrared light is less than the second threshold, and in a case where the blink time period is greater than a second preset time period, determining that the user is in a fatigue state.

Optionally, determining whether the user is in a fatigue state based on the reflected intensity of the infrared light comprises: calculating the number of times that the intensity of the reflected infrared light is first less than the second threshold and then greater than the second threshold again within a third preset time period, and obtaining the number of times of blinks within the third preset time period according to the number of times that the intensity of the reflected infrared light is first less than the second threshold and then greater than the second threshold again within the third preset time period, and in a case where the number of times of blinks is greater than a third threshold, determining that the user is in a fatigue state.

According to another aspect of present disclosure, provided is an optical detection apparatus for detecting a fatigue state of a user, comprising: a photosensor for receiving an infrared light reflected from eyes of the user and outputting a light intensity detection signal; and a processing module for determining whether the user is in a fatigue state according to the light intensity detection signal outputted by the photosensor.

Optionally, the optical detection apparatus further comprises: a filtering component for receiving the infrared light reflected from the eyes of the user and supplying the reflected infrared light to the photosensor.

Optionally, the optical detection apparatus further comprises: a light emitting component for emitting an infrared light to the eyes of the user.

Optionally, the optical detection apparatus further comprises: a control circuit for causing the photosensor to receive infrared light reflected from the eyes of the user and to output the light intensity detection signal.

Optionally, determining, by the processing module, whether the user is in a fatigue state according to the light intensity detection signal outputted by the photosensor comprises: in a case where the time period during which the intensity of the reflected infrared light as derived from the light intensity detection signal is less than a first threshold lasts for a first preset time period, determining that the user is in a fatigue state.

Optionally, determining, by the processing module, whether the user is in a fatigue state according to the light intensity detection signal outputted by the photosensor comprises: calculating a time period during which the intensity of the reflected infrared light as derived from the light intensity detection signal is less than a second threshold, obtaining a blink time period according to the time period during which the intensity of the reflected infrared light is less than the second threshold, and in a case where the blink time period is greater than a second preset time period, determining that the user is in a fatigue state.

Optionally, determining, by the processing module, whether the user is in a fatigue state according to the light intensity detection signal outputted by the photosensor comprises: calculating the number of times that the intensity of the reflected infrared light as derived from the light intensity detection signal is first less than the second threshold and then greater than the second threshold again within a third preset time period, and obtaining the number of times of blinks within the third preset time period according to the number of times that the intensity of the reflected infrared light is first less than the second threshold and then greater than the second threshold again within the third preset time period, and in a case where the number of times of blinks is greater than a third threshold, determining that the user is in a fatigue state.

Optionally, the filtering component is an infrared light filtering layer, and the infrared light filtering layer and the photosensor are disposed on a first substrate; and the infrared light filtering layer covers a light incident surface of the photosensor.

Optionally, the light emitting component comprises one or more infrared light emitting devices, and is disposed in the infrared light emitting layer, the infrared light emitting layer is disposed on the first substrate or on a second substrate provided opposite to the first substrate, a light emitting surface of the infrared light emitting layer and a light incident surface of the photosensor are oriented in the same direction, and an orthographic projection of the infrared light emitting layer on the first substrate is outside an orthographic projection of the photosensor on the first substrate.

Optionally, the infrared light filtering layer, the photosensor, and the infrared light emitting layer are encapsulated between the first substrate and the second substrate.

Optionally, the light emitting component comprises a plurality of infrared light emitting devices, the photosensor comprises a plurality of photosensitive devices, and the control circuit comprises a gate line, an input line, an output line, and a plurality of first switching transistors and a plurality of second switching transistors. Each photosensitive device, each infrared light emitting device, each first switching transistor and each second switching transistor are one group, and the gate line, the input line, and the output line are common to each group. In each group, an output end of the infrared light emitting device is grounded, an input end of the infrared light emitting device is connected to a first electrode of the first switching transistor, a second electrode of the first switching transistor is connected to the input line, a gate of the first switch transistor is connected to the gate line; an input end of the photosensor is grounded, an output end of the photosensor is connected to a first electrode of the second switching transistor, a second electrode of the second switching transistor is connected to the output line, and a gate of the second switching transistor is connected to the gate line.

According to yet another aspect of present disclosure, provided is an optical detection device, comprising: a carrier and an optical detection apparatus, the optical detection apparatus being disposed on the carrier.

DETAILED DESCRIPTION OF THE EMBODIMENTS

In order to further explain the technical measures and functions adopted by the present disclosure for achieving the intended purpose, the specific implementations, structures, features and functions of the optical detection method, the optical detection apparatus, and the optical detection device provided in accordance with the present disclosure will be described in detail below with reference to the accompanying drawings and preferred embodiments, and the detailed description is as follows.

Although the following embodiments of the present disclosure employ the driver's fatigue driving state detection as an application scenario of the optical detection method, the optical detection apparatus, and the optical detection device, those skilled in the art will understand that this is merely shown as an example, not intended to limit the present disclosure, and other applications are also feasible, such as user's fatigue state detection when user surfs the Internet or user's fatigue state detection during learning.

Figure 1:
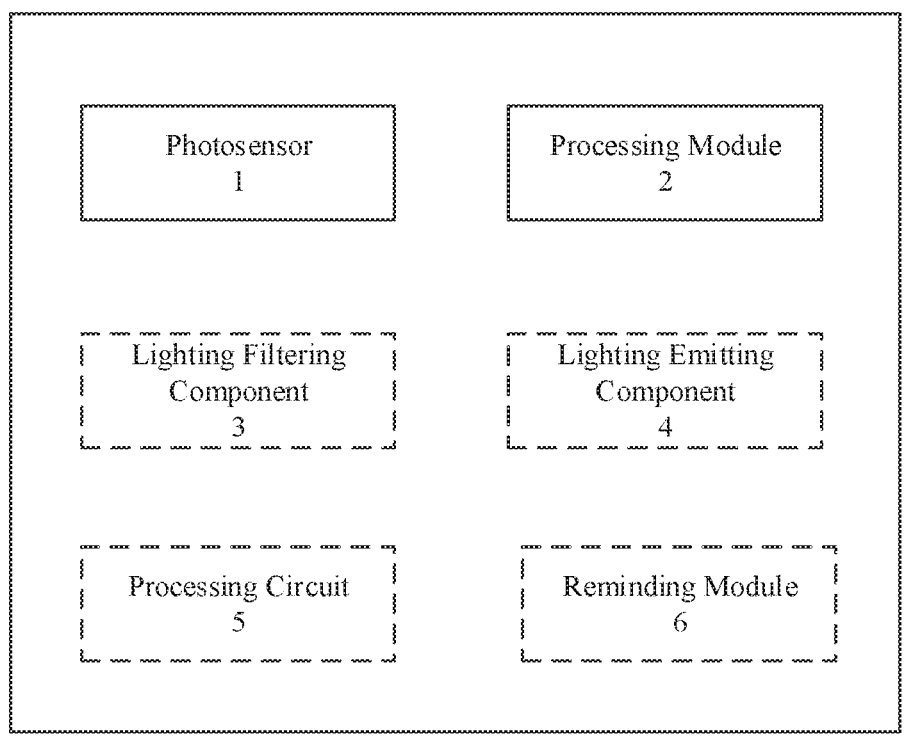
FIG. 1 is a schematic structure block diagram of an optical detection apparatus in accordance with an embodiment of the present disclosure.

FIG. 1 is a schematic structure block diagram of an optical detection apparatus in accordance with an embodiment of the present disclosure.

As shown in this figure, the optical detection apparatus comprises a photosensor 1 and a processing module 2. The photosensor 1 is for receiving infrared light reflected from eyes of a user and outputting a light intensity detection signal, and the processing module 2 is for determining whether the user is in a fatigue state according to the light intensity detection signal outputted by the photosensor. The processing module may include, but not limited to, a microprocessor, a micro control unit (MCU), and the like.

Optionally, the optical detection apparatus further comprises a filtering component 3 for receiving infrared light reflected from the eyes of the user and supplying the reflected infrared light to the photosensor 1.

Optionally, the optical detection apparatus further comprises a light emitting component 4 for emitting an infrared light to the eyes of the user.

Optionally, the optical detection apparatus further comprises a control circuit 5 for causing the photosensor 1 to receive infrared light reflected from the eyes of the user and to output a light intensity detection signal.

Optionally, the optical detection apparatus 100 further comprises a reminding module 6 connected to the processing module 2 and used for performing a reminding operation when the processing module 2 determines that the user is in a fatigue state. The reminding module 6 may include an LED light, a buzzer, and the like.

In the embodiment of the present disclosure, determining, by the processing module 2, whether the user is in a fatigue state according to the light intensity detection signal outputted by the photosensor comprises: in a case where the time period during which the intensity of the reflected infrared light as derived from the light intensity detection signal is less than a first threshold lasts for a first preset time period, determining that the user is in a fatigue state; calculating a time period during which the intensity of the reflected infrared light as derived from the light intensity detection signal is less than a second threshold, obtaining a blink time period according to the calculated time period during which the intensity of the reflected infrared light is less than the second threshold, and in a case where the blink time period is greater than a second preset time period, determining that the user is in a fatigue state; and/or, calculating the number of times that the intensity of the reflected infrared light as derived from the light intensity detection signal is first less than the second threshold and then greater than the second threshold again within a third preset time period, obtaining a number of times of blinks according to the number of times that the intensity of the reflected infrared light is first less than the second threshold and then greater than the second threshold again within the third preset time period, and in a case where the number of times of blinks is greater than a third threshold, determining that the user is in a fatigue state.

A specific structure of the optical detection apparatus in accordance with an embodiment of the present disclosure will be described below with reference to FIGS. 2 and 3. In this embodiment, the filtering component 3 is an infrared light filtering layer. However, those skilled in the art will understand that this is shown by way of example only, and other options are also feasible.

Figure 2:
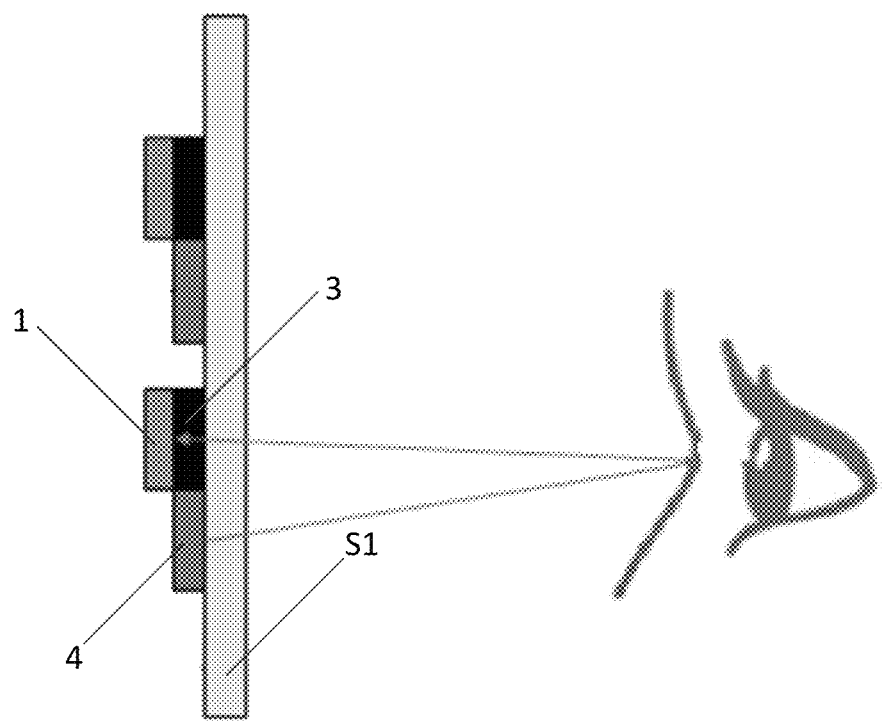
FIG. 2 is a schematic structural diagram of an optical detection apparatus in accordance with an embodiment of the present disclosure.

As shown in FIG. 2, the optical detection apparatus provided by an embodiment of the present disclosure comprises: a first substrate S1, a photosensor 1, and an infrared light filtering layer 3 The infrared light filtering layer 3 and the photosensor 1 are disposed on the first substrate S1, and the infrared light filtering layer 3 covers a light incident surface of the photosensor 1.

The optical detection apparatus is used to detect whether the driver is in a fatigue driving state, so as to improve vehicle driving safety of the driver. The optical detection apparatus may be disposed on the vehicle, for example, on a vehicle rearview mirror, a windshield, etc., and it may also serve as a wearable device to be worn on the driver, for example, glasses, and the like, no specific limitations are made herein. In addition, when the optical detection apparatus is used to detect whether the user is in a fatigue state when surfing the Internet, the optical detection apparatus may be disposed on the computer screen, or may be worn on the user as a wearable device, such as glasses, and the like.

The first substrate S1 serves as a main body supporting structure of the optical detection apparatus, and can fix other structures supporting the optical detection apparatus. The infrared light filtering layer 3 is disposed on one side of the first substrate S1, and may be distributed in a matrix. The photosensor 1 is disposed on the side of the infrared light filtering layer 3 that faces away from the first substrate S1, as shown in FIG. 2, and it can detect the intensity of the incident infrared light. The infrared light filtering layer 3 may be bonded to one side of the first substrate S1, and the light irradiated to the other side of the first substrate S1 can transmit through the first substrate S1 and be irradiated onto the infrared light filtering layer 3. Because the infrared light filtering layer 3 can allow the infrared light to transmit but block other light in the natural light, the infrared light can transmit through the first substrate S1 and the infrared light filtering layer 3 in sequence to be irradiated onto the photosensor 1.

Those skilled in the art will understand that, the photosensor 1 and the infrared light filtering layer 3 may be disposed on the same side of the first substrate S1 as shown in FIG. 2, or may also be disposed on two sides of the first substrate S1 separately. In addition, the infrared light filtering layer 3 may be disposed on the side of the photosensor 1 that faces the first substrate S1 as shown in FIG. 2, or may also be disposed on the side of the photosensor that faces away from the first substrate S1. The photosensor 1 and the infrared light filtering layer 3 may be arranged in various manners, no specific limitations are made herein, the only requirement that needs to be met is that the infrared light transmitting through the infrared light filtering layer 3 can be irradiated onto the photosensor 1 so that the photosensor 1 can detect the intensity of the infrared light.

The photosensor 1 is used to detect the intensity of infrared light. When the infrared light is irradiated onto the photosensor 1, the photosensor 1 can generate a current as a light intensity detection signal. The greater the intensity of the infrared light irradiated onto the photosensor 1 is, the larger the current generated by the photosensor 1 is; and the smaller the intensity of the infrared light irradiated onto the photosensor 1 is, the smaller the current generated by the photosensor 1 is. Therefore, in the embodiment of the present disclosure, the intensity of the infrared light reflected by the driver's eyes can be indirectly detected by detecting the magnitude of the current generated by the photosensor 1, so that an opening degree of the eyes can be determined, which will be described in detail later. The detection process using the above optical detection apparatus is as follows.

First, the eyes of the driver are irradiated with an infrared light. Because the infrared light is invisible light, irradiating the eyes of the driver with the infrared light has a relatively small influence to the eyes.

Next, the infrared light can be reflected after irradiating to the eyes, and the reflected infrared light can be irradiated onto the optical detection apparatus. Taking the optical detection apparatus shown in FIG. 2 as an example, the reflected infrared light sequentially transmits through the first substrate S1 and the infrared light filtering layer 3 of the optical detection apparatus and are irradiated onto the photosensor 1. An opening size of the eyes can be determined through the light intensity detection signal (corresponding to the intensity of the reflected infrared light) outputted from the photosensor 1, because, as for the infrared light with the same intensity that is irradiated to the eyes, the larger the open area of the eyes (i.e., the naked eye area) is, the larger the light intensity detection signal is, the smaller the open area of the eyes is, the smaller the light intensity detection signal is. Therefore, according to the light intensity detection signal outputted from the photosensor 1, the opening degree of eyes of the driver can be determined, and further it is determined whether the driver is in a fatigue driving state. The driver can be reminded in turn in a case where it is determined that the driver is in a fatigue driving state so as to ensure driving safety of the driver. The specific determination method will be further described later.

Optionally, the infrared light irradiated on the eyes may come from natural light. By irradiating the eyes with natural light, infrared light in the natural light can be reflected by the eyes and the reflected infrared light can be irradiated onto the photosensor 1, and the opening degree of the eyes can be determined based on the light intensity detection signal outputted from the photosensor 1.

Optionally, the optical detection apparatus described above may use infrared light of other sources in addition to infrared light from natural light.

For example, the optical detection apparatus described above comprises a light emitting component 4 as a light source. The light emitting component 4 comprises one or more infrared light emitting devices, and is disposed as an infrared light emitting layer. In the following, the light emitting component and the infrared light emitting layer are used indiscriminately. The infrared light emitting layer 4 is disposed on the first substrate S1, a light emitting surface of the infrared light emitting layer 4 and a light incident surface of the photosensor 1 are oriented in the same direction, that is, the side of the infrared light emitting layer 4 close to the eyes serves as the light emitting surface of the infrared light emitting layer 4, and the side of the photosensor 1 close to the eyes serves as the light incident surface of the photosensor 1. Optionally, the orthographic projection of the infrared light emitting layer 4 on the first substrate S1 is outside the orthographic projection of the photosensor 1 on the first substrate S1, so that the infrared light emitting layer 4 and the photosensor 1 are not overlapped with each other, thereby ensuring sufficient sensitization of the photosensor 1. Further, the infrared light filtering layer 3 and the infrared light emitting layer 4 do not overlap either.

In an embodiment of the present disclosure, the infrared light emitting layer 4 is used to emit an infrared light and to irradiate the infrared light to the eyes of the driver. Because the infrared light filtering layer 3 and the infrared light emitting layer 4 are not overlapped, the influence caused by the infrared light filtering layer 3 on the infrared light emitting layer 4 can be reduced. The infrared light emitted from the infrared light emitting layer 4 can transmit through the first substrate S1 and be irradiated to the eyes of the driver, and because the eyes can reflect the infrared light, the infrared light can be irradiated again onto the photosensor 1 after being reflected by the eyes. The photosensor 1 can detect the intensity of the reflected infrared light, and output a light intensity detection signal. The light intensity detection signal can be used to determine the opening size of eyes, and further determine whether the driver is in a fatigue driving state.

Optionally, the photosensor 1, the infrared light emitting layer 4 and the infrared light filtering layer 3 are disposed on the same side of the first substrate S1, the photosensor 1 is disposed on one side of the infrared light filtering layer 3 facing away from the first substrate S1; the infrared light emitting layer 4 and the infrared light filtering layer 3 are arranged side by side without overlapping each other.

By arranging the photosensor 1, the infrared light emitting layer 4, and the infrared light filtering layer 3 on the same side of the first substrate S1, on the one hand, it facilitates manufacturing setting of the optical detection apparatus, and on the other hand, the photosensor 1, the infrared light emitting layer 4, and the infrared light filtering layer 3 can be effectively protected by the first substrate S1, thereby improving the service life. Of course, the infrared light emitting layer 4 may be also disposed on the side of the first substrate S1 facing away from the infrared light filtering layer 3, in addition to being disposed on the side of the first substrate S1 facing the infrared light filtering layer 3.

Hence, with the optical detection apparatus in accordance with the embodiment of the present disclosure, accuracy of the detection of the driver's fatigue driving can be improved, because in the prior art, the optical detection apparatus generally detects the grip force on the steering wheel and determines the driver's fatigue degree through the magnitude of the grip force, in which accuracy of this optical detection apparatus is low. In the detection process adopting the optical detection apparatus in accordance with the embodiment of the present disclosure, the driver's eyes are irradiated with infrared light, and the opening size of eyes is determined based on the light intensity detection signal outputted by the photosensor 1, thereby determining the driver's driving fatigue degree, which improves accuracy of the detection. Moreover, by means of setting the infrared light emitting layer 4, an emission intensity of the infrared light can be increased, thereby the intensity of the infrared light irradiated to the photosensor 1 after being reflected by the eyes is increased, so that when the opening size of the eyes changes, the intensity of the reflected infrared light as detected on the photosensor 1 changes greatly, which in turn further improves accuracy of the optical detection apparatus for fatigue driving detection.

Figure 3:
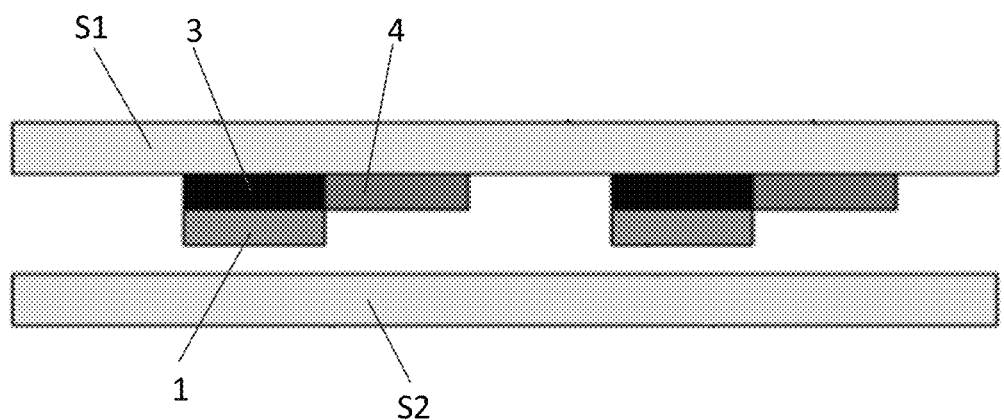
FIG. 3 is another schematic structural diagram of an optical detection apparatus in accordance with an embodiment of the present disclosure.

As shown in FIG. 3, in the optical detection apparatus provided by the embodiment of the present disclosure, in addition to the components described with reference to FIG. 2, the optical detection apparatus may further comprise: a second substrate S2. The second substrate S2 is disposed on a side opposite to the first substrate S1, and is encapsulated with the first substrate S1, so that the infrared light filtering layer 3, the photosensor 1, and the infrared light emitting layer 4 are encapsulated between the first substrate S1 and the second substrate S2.

Optionally, the second substrate S2 and the first substrate S1 may be encapsulated by a sealant, so that the infrared light emitting layer 4, the photosensor 1, and the infrared light filtering layer 3 are encapsulated between the first substrate S1 and the second substrate S2. Because the edges of the first substrate S1 and the second substrate S2 are sealed by the sealant, external debris can be prevented from entering the space between the first substrate S1 and the second substrate S2, which improves service life of the optical detection apparatus.

The infrared light emitting layer 4, the infrared light filtering layer 3, and the photosensor 1 described above may be disposed on the first substrate S1 and the second substrate S2 in various manners. Optionally, the infrared light emitting layer 4 and the infrared light filtering layer 3 are fixed on the first substrate S1, and the photosensor 1 is fixed on the second substrate S2. In the practical manufacturing process, the first substrate S1 and the second substrate S2 may be produced simultaneously, which improves production efficiency of the optical detection apparatus, and reduces thickness of a single substrate, and increases quality of the substrate.

The infrared light emitting layer 4, the infrared light filtering layer 3, and the photosensor 1 described above may be disposed on the first substrate S1 and the second substrate S2 in multiple manners. Optionally, as shown in FIG. 2, the infrared light emitting layer 4, the infrared light filtering layer 3, and the photosensor 1 are all fixed on the first substrate S1. In the meantime, because the infrared light filtering layer 3 is used to filter light other than infrared light in the natural light, in order to allow only infrared light to be irradiated onto the photosensor 1, it is necessary to ensure that the photosensor 1 and the infrared light filtering layer 3 correspond to each other. Thus, as shown in FIG. 3, the photosensor 1 and the infrared light filtering layer 3 are disposed overlapped on the first substrate S1, so that the photosensor 1 and the infrared light filtering layer 3 can be in one-on-one correspondence on the first substrate S1, thereby improving accuracy of the correspondence between the photosensor 1 and the infrared light filtering layer 3, which improves quality of the optical detection apparatus.

Figure 4:
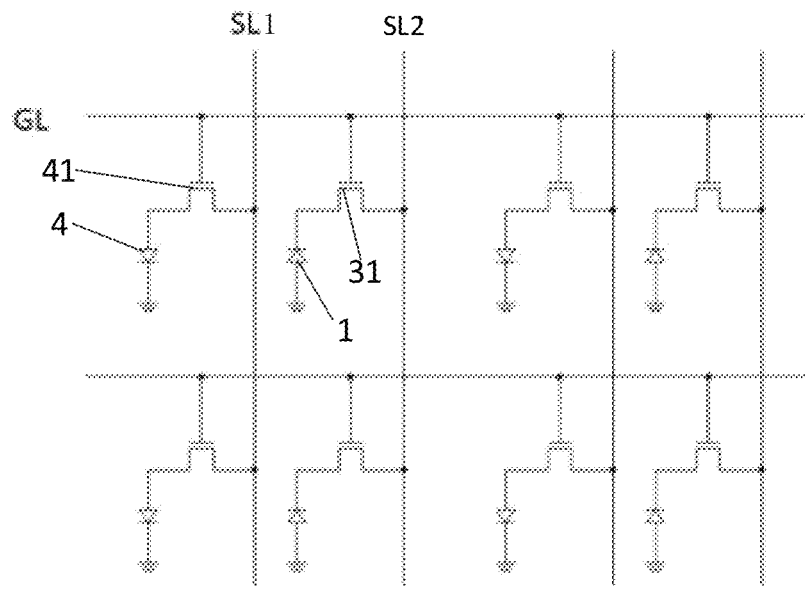
FIG. 4 is a circuit connection schematic diagram of a control circuit, a photosensor, and a light emitting component in an optical detection apparatus in accordance with an embodiment of the present disclosure.

Further, the optical detection apparatus provided by the embodiment of the present disclosure further comprises: a control circuit. FIG. 4 is a circuit connection schematic diagram of the control circuit 5, the light emitting component 4, and the photosensor 1 in the optical detection apparatus in accordance with an embodiment of the present disclosure. The light emitting component 4 includes a plurality of infrared light emitting devices, and the photosensor 1 includes a plurality of photosensitive devices.

The control circuit includes a gate line GL, an input line SL1, an output line SL2, a plurality of first switching transistors 41, and a plurality of second switching transistors 31. As shown in FIG. 4, the connection manner of the control circuit 5 with the light emitting component 4 and the photosensor 1 is as follows: each photosensitive device, each infrared light emitting device, each of the first switching transistors 41 and each of the second switching transistors 31 can be regarded as a group, and the gate line, the input line, and the output line are common to each group; in each group; an output end of the infrared light emitting device of the light emitting component 4 is grounded, an input end of the infrared light emitting device of the light emitting component 4 is connected to a first electrode of the first switching transistor 41, a second electrode of the first switching transistor 41 is connected to the input line SL1, a gate of the first switching transistor 41 is connected to the gate line GL; an input end of the photosensitive device of the photosensor 1 is grounded, an output end of the photosensitive device of the photosensor is connected to a first electrode of the second switching transistor 31, a second electrode of the second switching transistor 31 is connected to the output line SL2, and a gate of the second switching transistor 31 is connected to the gate line GL.

In a practical application process, when it needs to detect the fatigue state of the driver, the gate line GL can control each of the first switching transistors 41 and each of the second switching transistors 31 to be turned on, and the input line SL1 supplies a driving voltage to each infrared light emitting device of the infrared light emitting layer 4, so that the infrared light emitting layer 4 emits infrared light; the infrared light emitted by the infrared light emitting layer 4 are reflected by the driver's eyes and then irradiated onto the photosensor 1, and then each photosensitive device of the photosensor 1 generates a current signal, and each current signal is transmitted to the output line SL2; thereafter, the current signal flowing through the output line SL2 is transmitted as a light intensity detection signal to the subsequent processing module 2. The processing module 2 can determine an open degree of the driver's eyes based on intensity information of the current signal flowing through the output line SL2 (light intensity detection signal), to further determine the driver's fatigue state.

The specific process that the processing module 2 determines the fatigue state of the driver based on the light intensity detection signal (i.e., the current signal outputted by the photosensor, corresponding to the intensity of the infrared light reflected by the eyes) is described below.

In a case where the time period during which the light intensity detection signal is less than a first threshold lasts for a first preset time period, the processing module 2 determines that the driver is in a fatigue driving state, and controls the reminding module 6 to perform reminding. The first threshold may be a preset value. Optionally, the first threshold may be adapted according to each individual's eye size. Optionally, the first threshold may be adapted according to the intensity of the infrared light irradiated to the eyes.

Specifically, in the embodiment of the present disclosure, the processing module 2 acquires a light intensity detection signal (i.e., the current outputted from the photosensor) from the photosensor 1, and the light intensity detection signal is positively correlated with the intensity of reflected infrared light, and the intensity of the reflected infrared light is positively correlated with the opening area of the eyes (naked eye area) of the driver. In a case where the period during which the intensity of the reflected infrared light as derived from the light intensity detection signal is less than the first threshold lasts for the first preset time period (for example, 3 seconds), the processing module 2 can determine that the driver is in a fatigue driving state, the eyes are ready to close at any time for sleep, it is very dangerous, so the processing module 2 can control the reminding module 6 to perform reminding. The reminding module 6 may have various reminding manners, such as sound reminding, light reminding, vibration reminding etc., to remind the driver to stop quickly and take a break in time.

Additionally or alternatively, the processing module 2 is further configured to calculate a time period during which the intensity of the reflected infrared light as derived from the light intensity detection signal is less than a second threshold, and calculate a blink time period according to the time period during which the intensity of the reflected infrared light is less than the second threshold, and in a case where the blink time period is greater than a second preset time period, the processing module 2 controls the reminding module 7 to perform reminding. Similar to the first threshold, the second threshold is also a preset value. Meanwhile, the second threshold may be adapted according to each individual's eye size or may be adapted according to the intensity of the infrared light irradiated to the eyes.

Specifically, first, as described above, the light intensity detection signal (i.e., the current) obtained by the processing module 2 from the photosensor 1 is positively correlated with the intensity of reflected infrared light, and the intensity of the reflected infrared light is positively correlated with the opening area of the eyes (naked eye area) of the driver, so the processing module 2 can obtain the naked eye area information of the driver through the obtained light intensity detection signal. Second, when the driver blinks, the driver's naked eye area will rapidly become smaller and then rapidly become larger, thus, in the process when the driver's naked eye area rapidly becomes smaller and then rapidly becomes larger, the naked eye area will be less than a preset area during a small time period. This small time period can be regarded as the blink time period, and during this blink time period, the intensity of the reflected infrared light as derived from the light intensity detection signal will be first less than the second threshold and then greater than the second threshold again, so that the blink time period can be obtained according to the time period during which the intensity of the reflected infrared light is less than the second threshold. When the driver is in a fatigue driving state, the driver's blink speed will be slower and slower, and the calculated blink time period will be longer and longer. When the calculated blink time period is greater than the second preset time period (for example, 1 to 2 seconds), it can be determined that the driver is in a fatigue driving state, then the processing module 2 can control the reminding module 6 to perform reminding.

Additionally or alternatively, the processing module 2 is further configured to calculate the number of times that the intensity of the reflected infrared light as derived from the light intensity detection signal is first less than the second threshold and then greater than the second threshold again within a third preset time period, to obtain the number of times of blinks within a third preset time period according to the number of times that the light intensity detection signal is first less than the second threshold and then greater than the second threshold again within a third preset time period. In a case where the number of times of blinks is greater than a third threshold within a third preset time period, the processing module 2 controls the reminding module 6 to perform reminding. The third threshold is also a preset value corresponding to the number of times of blinks within the third preset time period when the driver is in a critical fatigue state.

Specifically, first, as described above, the light intensity detection signal (i.e., the current) obtained by the processing module 2 from the photosensor 1 is positively correlated with the intensity of reflected infrared light, and the intensity of the reflected infrared light is positively correlated with the opening area of the eyes (naked eye area) of the driver, so the processing module 2 can obtain the naked eye area information of the driver through the light intensity detection signal. Second, when the driver blinks, the driver's naked eye area will rapidly become smaller and then rapidly become larger, thus the intensity of the reflected infrared light as derived from the light intensity detection signal is also rapidly reduced and then rapidly increased. Thus the processing module 2 can obtain a blinking state of the driver through the change in light intensity detection signal, thereby obtain the number of times of blinks of the driver within the third preset time period. When the drivers are in a fatigue driving state, some drivers may relieve fatigue by constantly blinking, so the frequency of blinks will increase, accordingly, the processing module 2 can calculate the number of times of blinks within the third preset time period (e.g., 30 seconds) to determine the driver's fatigue driving state. In a case where the number of times of blinks is greater than a third threshold (e.g. more than 10 times), it shows that the driver is in a fatigue driving state, and the processing module 2 may control the reminding module 7 to perform reminding.

The embodiment of the present disclosure provides an optical detection apparatus for improving the accuracy of fatigue driving detection of the driver, while the optical detection apparatus in the prior art generally detects the grip force on the steering wheel, and determines the driver's fatigue degree by the magnitude of the grip force, accuracy of this detection manner is low. In the detection process using the optical detection apparatus in accordance with the embodiment of the present disclosure, the driver's eyes are irradiated with infrared light, and the processing module determines the opening size of the eyes according to the intensity detection signal outputted by the photosensor and positively associated with the intensity of the infrared light reflected by the eyes, thereby determining the driver's driving fatigue degree, which improves the detection accuracy. Moreover, when determining that the driver is in a fatigue driving state, the processor can control the reminding module to perform reminding, so as to further improve the safety.

In another aspect, an embodiment of the present disclosure further provides an optical detection device, comprising: a fixing carrier and an optical detection apparatus in accordance with the embodiment of the present disclosure, the optical detection apparatus being disposed on the fixing carrier, wherein the fixing carrier is a spectacle frame or a vehicle frame.

Optionally, the fixing carrier is a spectacle frame, the first substrate S1 of the optical detection apparatus is fixed on the spectacle frame as the spectacle lens. In this embodiment, each film layer of the optical detection apparatus is formed by an etching process, and is made of transparent material, therefore it does not affect the normal use of the spectacle lens. In addition, the wiring in the optical detection apparatus may be made of metal, such as gold, silver, aluminum, molybdenum, etc., the width of the wiring may be within 10 μm, and invisible to the naked eyes. In addition, in consideration of that a palpebral fissure length of the adult eyes is approximately 25 mm to 40 mm and a width thereof is approximately 10 mm to 12.5 mm, the photosensor may be arranged at the lens center corresponding to the eye position, corresponding to a spacing of 2 mm to 5 mm in the palpebral fissure length direction, a spacing of 0.5 mm to 1 mm in the palpebral fissure width direction, which can implement that the lens can have a very high transmittance without obstructing the line of sight under the premise of ensuring the detection accuracy.

Optionally, the fixing carrier is a vehicle frame, the optical detection apparatus is fixed as a rear view mirror on the vehicle frame. In this embodiment, when the driver drives the vehicle, the rear view mirror can face the eyes of the driver, which is convenient for detecting an opening degree of the eyes; in addition, the optical detection apparatus is integrated on the rear view mirror, which can save space and improve space utilization.

The embodiment of the present disclosure provides an optical detection device, for improving the accuracy of detection of the driver's fatigue driving, while the detection device in the prior art generally detects the grip force on the steering wheel, and the driver's fatigue degree is determined through the magnitude of the grip force, accuracy of this optical detection manner is low. In the detection process adopting the optical detection device in accordance with the embodiment of the present disclosure, the driver's eyes are irradiated with infrared light, and the opening size of the eyes is determined based on the light intensity detection signal that is outputted from the photosensor and is positively correlated to the intensity of the infrared light reflected by the eyes, thereby determining the driver's driving fatigue degree, which improves accuracy of the detection.

An optical detection method for optical detection method for a fatigue state in accordance with an embodiment of the present disclosure will be described in detail below with reference to FIG. 5. This method is applied to an optical detection apparatus in accordance with an embodiment of the present disclosure.

Figure 5:
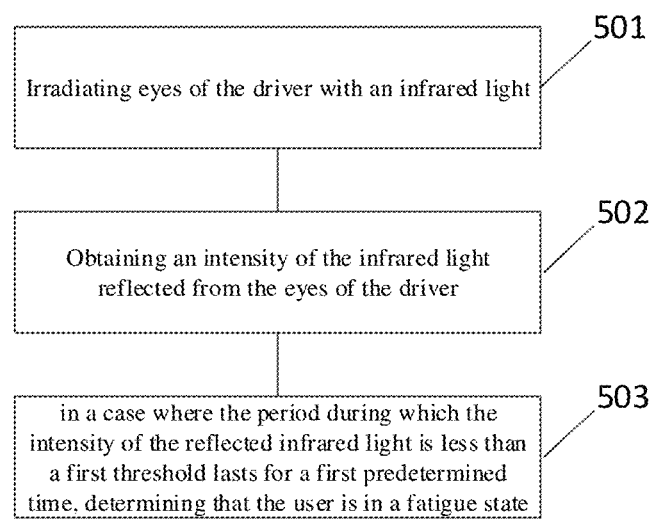
FIG. 5 is a flow chart of an optical detection method for a fatigue state in accordance with an embodiment of the present disclosure.

As shown in FIG. 5, the method comprises the following steps.

Step 501, eyes of the driver is irradiated with an infrared light.

Because the infrared light is invisible light, the driver's eyes being irradiated with infrared light will not affect the driver's field of vision, which ensures the driver's driving safety.

Optionally, the source of the infrared light may be various. For example, the infrared light that is irradiated to the driver's eyes may be from natural light or may be infrared light emitted from a light emitting component in the optical detection apparatus.

Step 502, an intensity of an infrared light reflected by the eyes of the driver is obtained.

Optionally, the intensity of the infrared light reflected by the driver's eyes is obtained by a photosensor, and a light intensity detection signal is outputted by the photosensor.

Specifically, the photosensor is used to detect the intensity of the infrared light reflected by the driver's eyes, and output a corresponding current signal as the light intensity detection signal. In more detail, when the reflected infrared light is irradiated onto the photosensor, the photosensor can generate a current signal, and the greater the intensity of the reflected infrared light is, the larger the intensity of the current generated by the photosensor is, i.e., the larger the outputted optical detection signal is; the smaller the intensity of the reflected infrared light is, the smaller the intensity of the current generated by the photosensor is, i.e., the smaller the outputted light intensity detection signal is. Therefore, the intensity of the reflected infrared light can be indirectly detected by detecting the magnitude of the current generated by the photosensor.

Step 503, it is determined whether the driver is in a fatigue state based on the intensity of the infrared light reflected, and the specific operations are: in a case where the time period during which the intensity of the infrared light reflected is less than a first threshold lasts for a first preset time, determining that the driver is in a fatigue state. Optionally, the first threshold may be a preset value. Optionally, the first threshold may be adapted according to each individual's eye size. Optionally, the first threshold may be adapted according to the intensity of the infrared light irradiated to the eyes.

Specifically, the light intensity detection signal is positively correlated with the intensity of reflected infrared light, and the intensity of the reflected infrared light is positively correlated with the opening area of the eyes (naked eye area) of the driver. In a case where the time period during which the intensity of the reflected infrared light is less than the first threshold lasts for the first preset time period, it indicates that the driver's eyes have been opened very small, and the eyes are ready to close for sleep at any time, and then it can be determined that the driver is in a fatigue state.

Optionally, the intensity of the reflected infrared light can be derived from the light intensity detection signal.

In addition, in the case, optically, reminding may be also performed.

Figure 6:
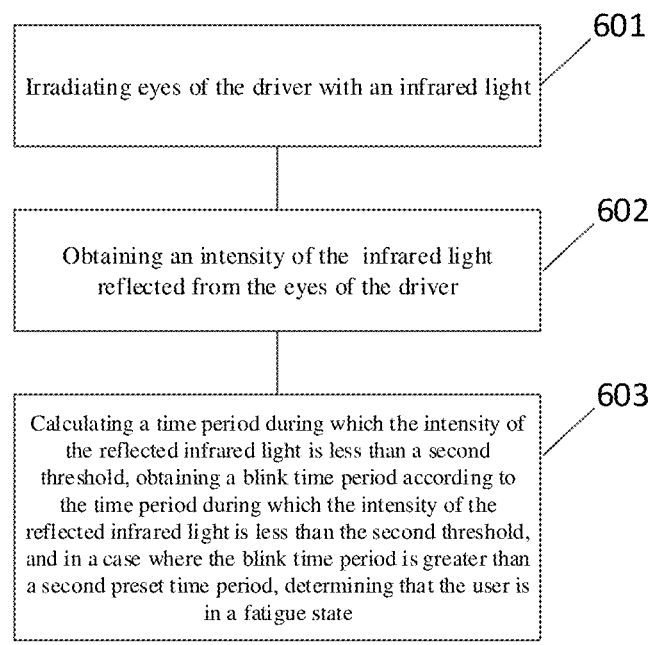
FIG. 6 is a flow chart of another optical detection method for a fatigue state in accordance with an embodiment of the present disclosure.

FIG. 6 is a flow chart of another optical detection method for a fatigue state in accordance with an embodiment of the present disclosure.

As shown in FIG. 6, steps 601 to 602 are the same as steps 501 to 502 described with reference to FIG. 5, and this another detection method further comprises the following steps.

Step 603, it is determined whether the driver is in a fatigue state based on the intensity of the infrared light reflected, and the specific operations are: calculating a time period during which the intensity of the infrared light reflected is less than a second threshold, obtaining a blink time period according to the time period during which the intensity of the infrared light reflected is less than the second threshold, and in a case the blink time period is greater than a second preset time period, determining that the user is in a fatigue state.

Similar to the first threshold, the second threshold is also a preset value. Meanwhile, the second threshold may be adapted according to each individual's eye size or may be adapted according to the intensity of the infrared light irradiated to the eyes.

Specifically, when the driver blinks, the driver's naked eye area will rapidly become smaller and then rapidly become larger again, in the process when the driver's naked eye area rapidly becomes smaller and then rapidly becomes larger again, the naked eye area will be less than a preset area during a small time period, this small time period can be regarded as a blink time period, and during this blink time period, the intensity of the reflected infrared light will be first less than the second threshold and then greater than the second threshold again, so the blink time period can be obtained according to the time period during which the intensity of the reflected infrared light is first less than the second threshold. When the driver is in a fatigue driving state, the driver's blink speed will be slower and slower, and the blink time period will be longer and longer, when the blink time period is greater than the second preset time period (for example, 1 to 2 seconds), it can be determined that the driver is in a fatigue driving state.

Optionally, the intensity of the reflected infrared light can be derived from the light intensity detection signal outputted by the photosensor.

In addition, in the case, optically, reminding may be also performed.

Figure 7:
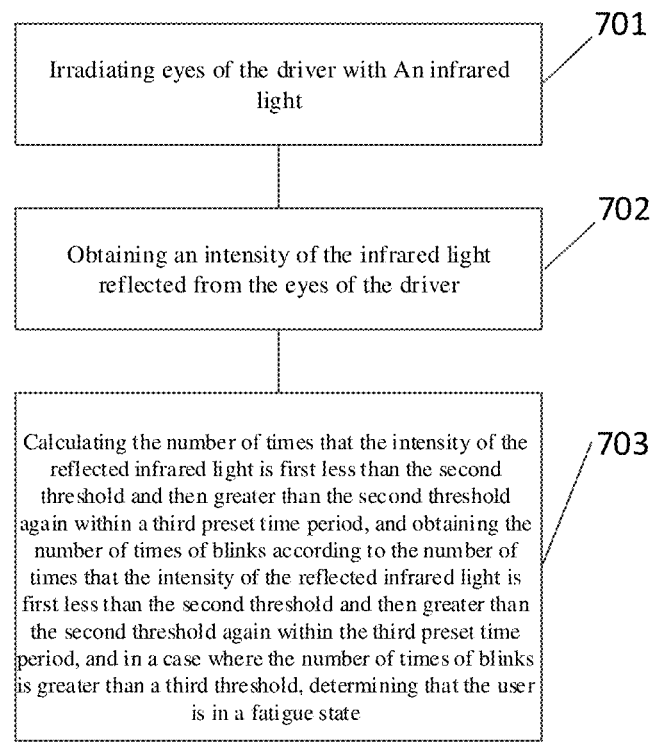
FIG. 7 is a flow chart of yet another optical detection method for a fatigue state in accordance with an embodiment of the present disclosure.

FIG. 7 is a flow chart of another optical detection method for a fatigue state in accordance with an embodiment of the present disclosure.

As shown in FIG. 7, steps 701 to 702 are the same as steps 501 to 502 described with reference to FIG. 5, and this another detection method further comprises the following steps.

Step 703, it is determined whether the driver is in a fatigue state based on the intensity of the infrared light reflected, and the specific operations are: calculating the number of times that the intensity of the infrared light reflected is first less than the second threshold and then greater than the second threshold again within a third preset time period, and obtaining the number of times of blinks within the third preset time period according to the number of times that the infrared light reflected is first less than the second threshold and then greater than the second threshold again within a third preset time period, and in a case where the number of times of blinks is greater than a third threshold, determining that the driver is in a fatigue state.

Optionally, the intensity of the reflected infrared light can be derived from the light intensity detection signal outputted by the photosensor.

Similar to the first threshold, the second threshold is also a preset value. Meanwhile, the second threshold may be adapted according to each individual's eye size or may be adapted according to the intensity of the infrared light that are irradiated to the eyes. The third threshold is also a preset value corresponding to the number of times of blinks within the third preset time period when the driver is in a critical fatigue state.

Specifically, as described above, a blinking state of the driver can be obtained through the change of the intensity of the infrared light reflected, and further the number of times of blinks of the driver within the third preset time period can be obtained. When the driver is in a fatigue driving state, the frequency of blinks will increase, the number of times of blinks within the third preset time period (e.g., 30 seconds) can be calculated to determine the driver's fatigue driving state, and in a case where the number of times of blinks is greater than a third threshold (e.g., 10 times), it shows that the driver is a fatigue driving state.

It should be noted that although three detection methods are respectively described with reference to FIGS. 5 to 7, the three detection methods are not necessarily performed independently, but may be combined with each other. For example, in order to further improve accuracy of the detection, when it is determined that the period during which the intensity of the reflected infrared light is less than the first threshold lasts for the first preset time period as described in step 503, it is also possible to further determine whether the blink time period is greater than the second preset time period as described in step 603, or to further determine whether the number of times of blinks within the third preset time period is greater than the third threshold as described in step 703, and finally obtain a determination result as to whether the driver is in a fatigue driving state.

The embodiment of the present disclosure provides a detection method for fatigue driving, which is applied to an optical detection apparatus. In the prior art, generally the grip force on the steering wheel is detected, and a fatigue degree of the driver is determined by the magnitude of the grip force, but accuracy of this detection manner is low. In the detection process using the optical detection method for a fatigue driving state in accordance with the embodiment of the present disclosure, the driver's eyes may be irradiated with infrared light, and the eyes opening size can be determined according to the intensity of the infrared light reflected by the eyes, further, the driver's driving fatigue degree is determined, which improves accuracy of the detection. Moreover, when it is determined that the driver is in a fatigue driving state, reminding can be performed, which further improves the safety.

The above are only specific implementations of the present disclosure, but the protection scope of the present disclosure is not limited thereto, changes or substitutions that can be easily conceived of by those skilled in the art within the technical range of the present disclosure should all fall into the protection scope of the present disclosure. Therefore, the protection scope of the present disclosure should be determined based on the protection scopes of the claims.

What is claimed is:

1. An optical detection apparatus for detecting a fatigue state of a user, comprising:
    a light emitting component for emitting an infrared light to the eyes of the user;
    a photosensor for receiving an infrared light reflected from eyes of the user and outputting a light intensity detection signal;
    a processing module for determining whether the user is in a fatigue state according to the light intensity detection signal outputted by the photosensor; and
    a control circuit for causing the photosensor to receive the infrared light reflected from eyes of the user and to output the light intensity detection signal,
    wherein, the photosensor comprises a plurality of photosensitive devices, the light emitting component comprises a plurality of infrared light emitting devices, and the control circuit comprises a plurality of switching transistors, a gate line, an input line, and an output line, and the plurality of switching transistors comprise a plurality of first switching transistors and a plurality of second switching transistors;
    wherein, each photosensitive device, each infrared light emitting device, each first switching transistor and each second switching transistor are one group, and the gate line, the input line, and the output line are common to each group,
    wherein, in each group, an output end of the infrared light emitting device is grounded, an input end of the infrared light emitting device is connected to a first electrode of the first switching transistor, a second electrode of the first switching transistor is connected to the input line, a gate of the first switch transistor is connected to the gate line; an input end of the photosensor is grounded, an output end of the photosensor is connected to a first electrode of the second switching transistor, a second electrode of the second switching transistor is connected to the output line, and a gate of the second switching transistor is connected to the gate line.

2. The optical detection apparatus according to claim 1, further comprising:
    a filtering component for receiving the infrared light reflected from eyes of the user and supplying the reflected infrared light to the photosensor.

3. The optical detection apparatus according to claim 1, wherein
    the processing module determining whether the user is in a fatigue state according to the light intensity detection signal outputted by the photosensor comprises:
    in a case where the time period during which the intensity of the reflected infrared light as derived from the light intensity detection signal is less than a first threshold lasts for a first preset time period, determining that the user is in a fatigue state.

4. The optical detection apparatus according to claim 1, wherein
    the processing module determining whether the user is in a fatigue state according to the light intensity detection signal outputted by the photosensor comprises:
    calculating a time period during which the intensity of the reflected infrared light as derived from the light intensity detection signal is less than a second threshold, obtaining a blink time period according to the time period during which the intensity of the reflected infrared light is less than the second threshold, and in a case where the blink time period is greater than a second preset time period, determining that the user is in a fatigue state.

5. The optical detection apparatus according to claim 1, wherein
    the processing module determining whether the user is in a fatigue state according to the light intensity detection signal outputted by the photosensor comprises:
    calculating the number of times that the intensity of the reflected infrared light as derived from the light intensity detection signal is first less than the second threshold and then greater than the second threshold again within a third preset time period, and obtaining the number of times of blinks within the third preset time period according to the number of times that the intensity of the reflected infrared light is first less than the second threshold and then greater than the second threshold again within the third preset time period, and in a case where the number of times of blinks is greater than a third threshold, determining that the user is in a fatigue state.

6. The optical detection apparatus according to claim 1, wherein the filtering component is an infrared light filtering layer, and the infrared light filtering layer and the photosensor are disposed on a first substrate; wherein the infrared light filtering layer covers a light incident surface of the photosensor.

7. The optical detection apparatus according to claim 6, wherein the light emitting component is disposed as an infrared light emitting layer, the infrared light emitting layer is disposed on the first substrate or on a second substrate provided opposite to the first substrate, a light emitting surface of the infrared light emitting layer and a light incident surface of the photosensor are oriented in the same direction, and an orthographic projection of the infrared light emitting layer on the first substrate is outside an orthographic projection of the photosensor on the first substrate.

8. The optical detection apparatus according to claim 7, wherein the infrared light filtering layer, the photosensor, and the infrared light emitting layer are encapsulated between the first substrate and the second substrate.

9. An optical detection device, comprising:
    a carrier and an optical detection apparatus according to claim 1, the optical detection apparatus being disposed on the carrier.

* * * * *